United States Patent
Iyer et al.

(10) Patent No.: US 8,593,816 B2
(45) Date of Patent: Nov. 26, 2013

(54) COMPACT CONNECTOR ASSEMBLY FOR IMPLANTABLE MEDICAL DEVICE

(75) Inventors: Rajesh V. Iyer, Eden Prairie, MN (US); Michael G. Marinkov, Woodbury, MN (US); Lea A. Nygren, Bloomington, MN (US); Jeffrey J. Clayton, Ramsey, MN (US); James Strom, Arden Hills, MN (US); Thomas E. Meyer, Stillwater, MN (US); Steven T. Deininger, Blaine, MN (US); Wayne R. Kuechenmeister, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 243 days.

(21) Appl. No.: 13/239,037

(22) Filed: Sep. 21, 2011

(65) Prior Publication Data

US 2013/0070423 A1 Mar. 21, 2013

(51) Int. Cl.
*H05K 7/00* (2006.01)
*A61N 1/00* (2006.01)

(52) U.S. Cl.
USPC ............ 361/728; 607/37; 607/38; 361/306.2; 361/307; 439/909

(58) Field of Classification Search
USPC ............. 361/306.2, 307, 728; 607/36, 37, 38; 439/909
See application file for complete search history.

(56) References Cited

U.S. PATENT DOCUMENTS

| | | | |
|---|---|---|---|
| 1,488,175 A | 3/1924 | Strandell | |
| 3,343,122 A | 9/1967 | Drogo | |
| 3,449,708 A | 6/1969 | Lawrence et al. | |
| 3,646,405 A | 2/1972 | Wallis et al. | |
| 3,803,875 A | 4/1974 | Root et al. | |
| 3,920,888 A | 11/1975 | Barr | |
| 4,152,540 A | 5/1979 | Duncan et al. | |
| 4,285,730 A | 8/1981 | Sanford et al. | |

(Continued)

FOREIGN PATENT DOCUMENTS

| | | |
|---|---|---|
| DE | 8631853 | 11/1988 |
| EP | 0404435 A1 | 12/1990 |

(Continued)

OTHER PUBLICATIONS

Angeloni et al., "Interference between GSM mobile phones and pace-makers: in vitro evaluation of interaction mechanisms," Engineering in Medicine and Biology Society, 2001 Proceedings of the 23rd Annual EMBS International Conference of the IEEE, vol. 4, Oct. 25-28, 2001, pp. 3985-3988.

(Continued)

*Primary Examiner* — Ramon Barrera
(74) *Attorney, Agent, or Firm* — Shumaker & Sieffert, P.A.

(57) ABSTRACT

A connector assembly for an implantable medical device includes a plurality of feedthroughs mounted in a conductive array plate, each feedthrough in the plurality of feedthroughs including a feedthrough pin electrically isolated from the conductive array plate by an insulator and an electronic module assembly including a plurality of conductive strips set in a non-conductive block. The plurality of conductive strips is in physical and electrical contact with the feedthrough pins at an angle of less than 135 degrees. The connector assembly further includes at least one circuit, the circuit including a plurality of conductors corresponding to the plurality of feedthroughs. The plurality of conductors of the circuit is in physical and electrical contact with a corresponding one of the conductive strips of the plurality of conductive strips of the electronic module assembly at an angle of less than 135 degrees.

33 Claims, 10 Drawing Sheets

(56) References Cited

U.S. PATENT DOCUMENTS

| | | |
|---|---|---|
| 4,314,031 A | 2/1982 | Sanford et al. |
| 4,323,654 A | 4/1982 | Tick et al. |
| 4,420,569 A | 12/1983 | Tick |
| 4,421,947 A | 12/1983 | Kyle |
| 4,424,551 A | 1/1984 | Stevenson et al. |
| 4,441,780 A | 4/1984 | Walters |
| 4,514,782 A | 4/1985 | Sakamoto et al. |
| 4,784,141 A | 11/1988 | Peers-Trevarton |
| 4,934,366 A | 6/1990 | Truex et al. |
| 4,940,858 A | 7/1990 | Taylor et al. |
| 4,943,686 A | 7/1990 | Kucharek |
| 4,966,564 A | 10/1990 | Foote |
| 4,997,380 A | 3/1991 | Etienne et al. |
| 5,012,807 A | 5/1991 | Stutz, Jr. |
| 5,015,530 A | 5/1991 | Brow et al. |
| 5,021,307 A | 6/1991 | Brow et al. |
| 5,033,095 A | 7/1991 | Marcantonio |
| 5,089,446 A | 2/1992 | Cornelius et al. |
| 5,104,738 A | 4/1992 | Brow et al. |
| 5,104,755 A | 4/1992 | Taylor et al. |
| 5,175,067 A | 12/1992 | Taylor et al. |
| 5,242,097 A | 9/1993 | Socha |
| 5,251,986 A | 10/1993 | Arena |
| 5,294,241 A | 3/1994 | Taylor et al. |
| 5,306,581 A | 4/1994 | Taylor et al. |
| 5,333,095 A | 7/1994 | Stevenson et al. |
| 5,336,246 A | 8/1994 | Dantanarayana |
| 5,406,444 A | 4/1995 | Selfried et al. |
| 5,531,003 A | 7/1996 | Seifried et al. |
| 5,573,000 A | 11/1996 | Goffer et al. |
| 5,648,302 A | 7/1997 | Brow et al. |
| 5,650,759 A | 7/1997 | Hittman et al. |
| 5,662,692 A | 9/1997 | Paspa et al. |
| 5,693,580 A | 12/1997 | Brow et al. |
| 5,751,539 A | 5/1998 | Stevenson et al. |
| 5,817,984 A | 10/1998 | Taylor et al. |
| 5,821,011 A | 10/1998 | Taylor et al. |
| 5,825,608 A | 10/1998 | Duva et al. |
| 5,851,222 A | 12/1998 | Taylor et al. |
| 5,866,851 A | 2/1999 | Taylor et al. |
| 5,867,361 A | 2/1999 | Wolf et al. |
| 5,870,272 A | 2/1999 | Seifried et al. |
| 5,871,513 A | 2/1999 | Taylor et al. |
| 5,902,326 A | 5/1999 | Lessar et al. |
| 5,905,627 A | 5/1999 | Brendel et al. |
| 5,957,364 A | 9/1999 | Socha |
| 6,031,710 A | 2/2000 | Wolf et al. |
| 6,076,017 A | 6/2000 | Taylor et al. |
| 6,090,503 A | 7/2000 | Taylor et al. |
| 6,248,080 B1 | 6/2001 | Miesel et al. |
| 6,275,369 B1 | 8/2001 | Stevenson et al. |
| 6,349,025 B1 | 2/2002 | Fraley et al. |
| 6,414,835 B1 | 7/2002 | Wolf et al. |
| 6,453,551 B1 | 9/2002 | Nordquist et al. |
| 6,519,133 B1 | 2/2003 | Eck et al. |
| 6,529,103 B1 | 3/2003 | Brendel et al. |
| 6,536,882 B1 | 3/2003 | Hawkins et al. |
| 6,566,978 B2 | 5/2003 | Stevenson et al. |
| 6,574,508 B2 | 6/2003 | Zaouali et al. |
| 6,603,182 B1 | 8/2003 | Low et al. |
| 6,643,903 B2 | 11/2003 | Stevenson et al. |
| 6,660,116 B2 | 12/2003 | Wolf et al. |
| 6,759,163 B2 | 7/2004 | Frysz et al. |
| 6,759,309 B2 | 7/2004 | Gross |
| 6,765,779 B2 | 7/2004 | Stevenson et al. |
| 6,765,780 B2 | 7/2004 | Brendel et al. |
| 6,767,779 B2 | 7/2004 | Tanghe et al. |
| 6,768,629 B1 | 7/2004 | Allen et al. |
| 6,778,040 B2 | 8/2004 | Kim |
| 6,835,084 B2 | 12/2004 | Poon et al. |
| 6,855,456 B2 | 2/2005 | Taylor et al. |
| 6,862,478 B1 | 3/2005 | Goldstein |
| 6,882,248 B2 | 4/2005 | Stevenson et al. |
| 6,888,233 B2 | 5/2005 | Horning et al. |
| 6,888,715 B2 | 5/2005 | Stevenson et al. |
| 6,924,165 B2 | 8/2005 | Horning et al. |
| 6,936,899 B2 | 8/2005 | Juengling |
| 6,985,347 B2 | 1/2006 | Stevenson et al. |
| 6,985,349 B2 | 1/2006 | Smyth et al. |
| 6,987,428 B2 | 1/2006 | Marketkar et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,035,076 B1 | 4/2006 | Stevenson |
| 7,035,077 B2 | 4/2006 | Brendel |
| 7,038,900 B2 | 5/2006 | Stevenson et al. |
| 7,046,499 B1 | 5/2006 | Imani et al. |
| 7,094,967 B2 | 8/2006 | Evans et al. |
| 7,098,117 B2 | 8/2006 | Najafi et al. |
| 7,110,827 B2 | 9/2006 | Sage et al. |
| 7,187,535 B1 | 3/2007 | Iyer et al. |
| 7,199,995 B2 | 4/2007 | Stevenson |
| 7,210,966 B2 | 5/2007 | Taylor et al. |
| 7,214,441 B2 | 5/2007 | Cortright et al. |
| 7,260,434 B1 | 8/2007 | Lim et al. |
| 7,274,964 B2 | 9/2007 | Balsells |
| 7,281,305 B1 | 10/2007 | Iyer et al. |
| 7,285,509 B2 | 10/2007 | Bayya et al. |
| 7,310,216 B2 | 12/2007 | Stevenson et al. |
| 7,502,217 B2 | 3/2009 | Zhao et al. |
| 7,706,124 B2 | 4/2010 | Zhao et al. |
| 7,725,190 B2 | 5/2010 | Iyer et al. |
| 7,803,014 B2 | 9/2010 | Sprain et al. |
| 7,916,448 B2 | 3/2011 | Zhao et al. |
| 7,917,218 B2 | 3/2011 | Iyer et al. |
| 2001/0050837 A1 | 12/2001 | Stevenson et al. |
| 2002/0166618 A1 | 11/2002 | Wolf et al. |
| 2003/0071016 A1 | 4/2003 | Shih et al. |
| 2003/0083715 A1 | 5/2003 | Taylor et al. |
| 2003/0123215 A1 | 7/2003 | Allen et al. |
| 2003/0125185 A1 | 7/2003 | Hirose |
| 2003/0163171 A1 | 8/2003 | Kast et al. |
| 2003/0179536 A1 | 9/2003 | Stevenson et al. |
| 2004/0034393 A1 | 2/2004 | Hansen et al. |
| 2004/0093038 A1 | 5/2004 | Biggs et al. |
| 2004/0126953 A1 | 7/2004 | Cheung |
| 2004/0152229 A1 | 8/2004 | Najafi et al. |
| 2004/0167582 A1 | 8/2004 | Tvaska et al. |
| 2004/0180464 A1 | 9/2004 | Horning et al. |
| 2004/0220627 A1 | 11/2004 | Crespi et al. |
| 2004/0244484 A1 | 12/2004 | Horning et al. |
| 2004/0257747 A1 | 12/2004 | Stevenson et al. |
| 2005/0060003 A1 | 3/2005 | Taylor et al. |
| 2005/0092507 A1 | 5/2005 | Marshall et al. |
| 2005/0095352 A1 | 5/2005 | Marshall et al. |
| 2005/0186823 A1 | 8/2005 | Ring et al. |
| 2005/0197677 A1 | 9/2005 | Stevenson |
| 2005/0201039 A1 | 9/2005 | Stevenson et al. |
| 2005/0248907 A1 | 11/2005 | Stevenson et al. |
| 2006/0009813 A1 | 1/2006 | Taylor et al. |
| 2006/0085043 A1 | 4/2006 | Stevenson |
| 2006/0167522 A1 | 7/2006 | Malinowski |
| 2006/0173506 A1 | 8/2006 | Rusin et al. |
| 2006/0192272 A1 | 8/2006 | Receveur et al. |
| 2006/0221543 A1 | 10/2006 | Stevenson et al. |
| 2006/0247714 A1 | 11/2006 | Taylor et al. |
| 2006/0259093 A1 | 11/2006 | Stevenson et al. |
| 2006/0290257 A1 | 12/2006 | Heo et al. |
| 2007/0004580 A1 | 1/2007 | Kass |
| 2007/0019362 A1 | 1/2007 | Stevenson et al. |
| 2007/0043399 A1 | 2/2007 | Stevenson et al. |
| 2007/0179553 A1 | 8/2007 | Iyer et al. |
| 2007/0179554 A1 | 8/2007 | Iyer et al. |
| 2007/0179555 A1 | 8/2007 | Iyer et al. |
| 2007/0217121 A1 | 9/2007 | Fu et al. |
| 2007/0234540 A1 | 10/2007 | Iyer et al. |
| 2007/0239223 A1 | 10/2007 | Engmark et al. |
| 2007/0260282 A1 | 11/2007 | Taylor et al. |
| 2008/0060844 A1 | 3/2008 | Teske et al. |
| 2008/0118831 A1 | 5/2008 | Jouanneau-Si-Larbi et al. |
| 2008/0208278 A1 | 8/2008 | Janzig et al. |
| 2009/0079517 A1 | 3/2009 | Iyer |

(56) References Cited

U.S. PATENT DOCUMENTS

2009/0079518 A1 3/2009 Iyer
2009/0079519 A1 3/2009 Iyer
2010/0009512 A1 1/2010 Fishburn
2010/0179606 A1 7/2010 Iyer
2010/0326723 A1 12/2010 McCusker et al.

FOREIGN PATENT DOCUMENTS

EP  1400993 A1 3/2004
EP  1760735 A1 3/2007
WO  03073450 A1 9/2003
WO  2009039006 A1 3/2009

OTHER PUBLICATIONS

DIEMAT DM2995PF Series Lead (Pb)-Free Sealing Glass Preforms—Preliminary Data Sheet, Aug. 27, 2006, 4 pgs.
DIEMAT DM2700PF Series, DM2700PF/DM2760PF, Low-Temperature Sealing Glass Preforms—Product Data Sheet, Jul. 24, 2006, 4 pgs.
DIEMAT, Inc. Material Safety Data Sheet—DM2995PF, Aug. 23, 2006, 4 pgs.
Yourassowsky, et al., "Combination of minocycline and rifampicin against methicillin- and gentamicin-resistant *Staphylococcus aureus*," J. Clin Pathol 1981, 34, pp. 559-563.
Bayston et al., "Antimicrobial activity of silicone rubber used in hydrocephalus shunts, after impregnation with antimicrobial substances," J. Clin Pathol 1981, 34, pp. 1057-1062.

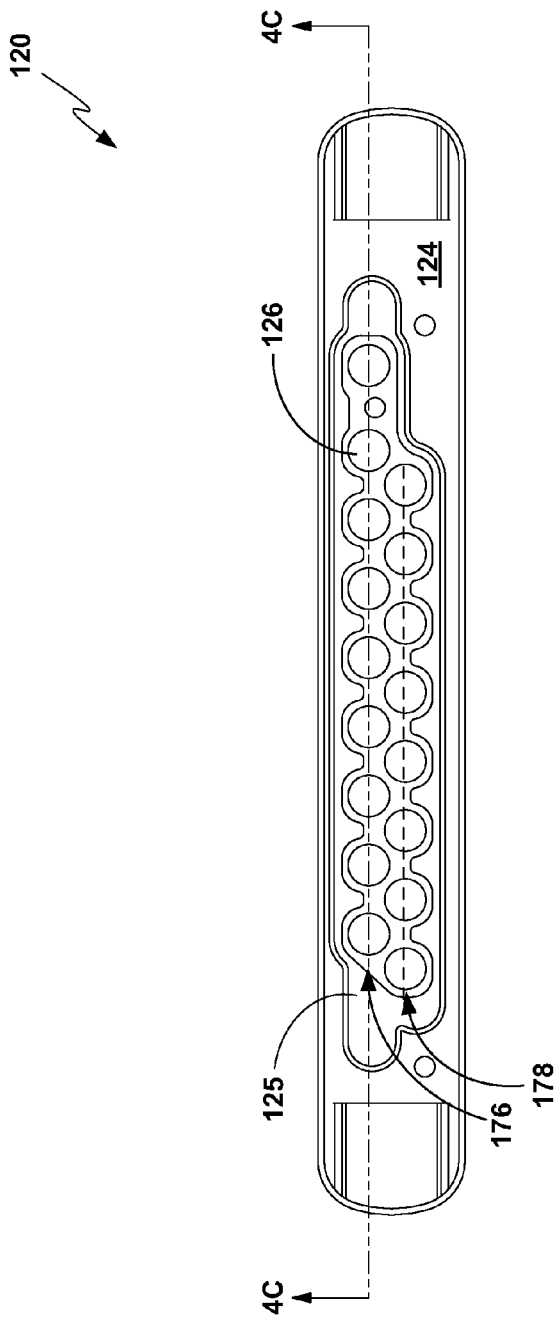
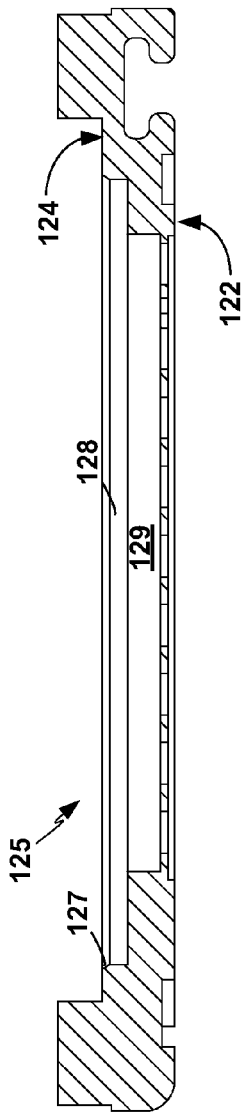
FIG. 4B
FIG. 4C

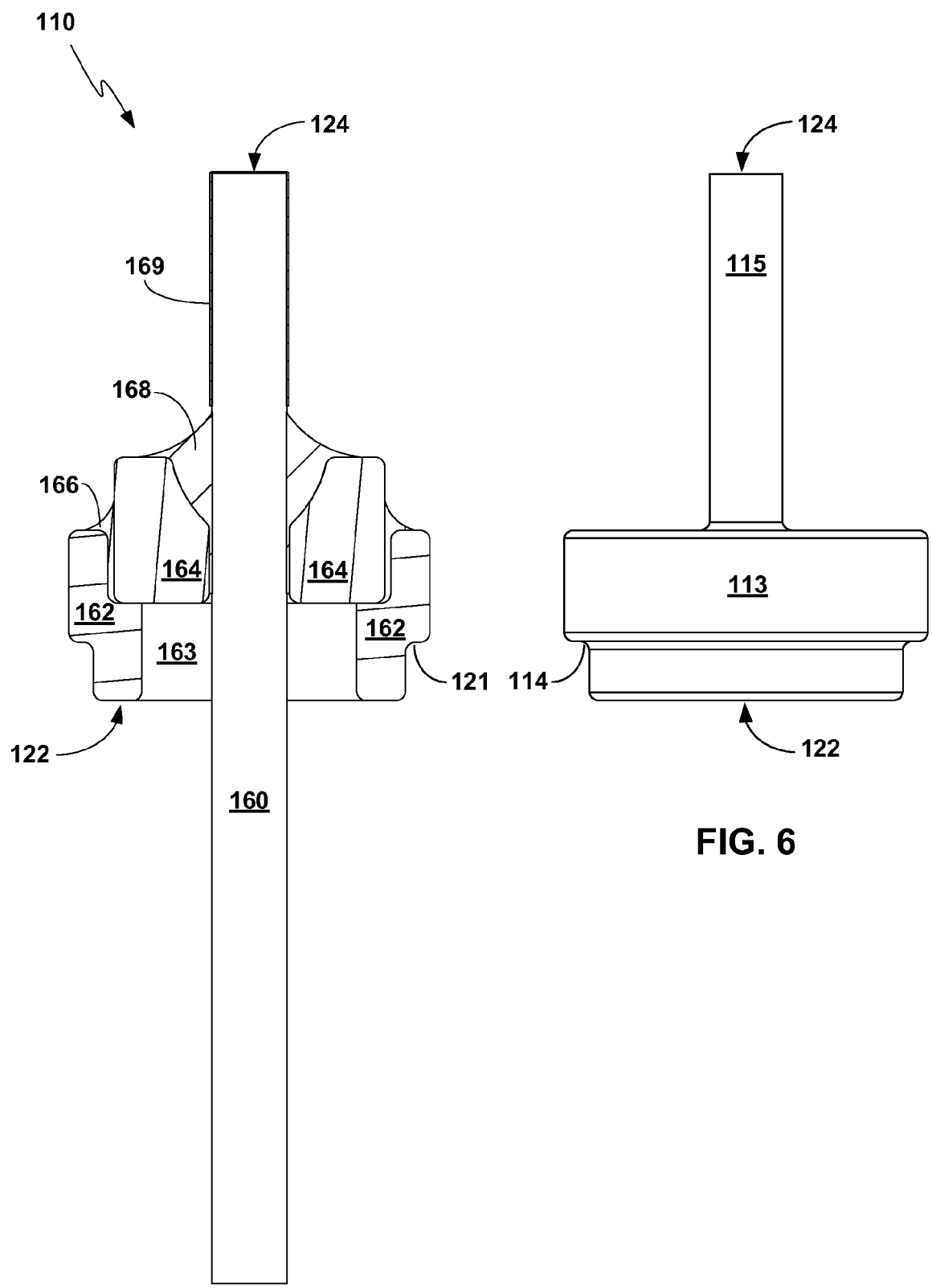

COMPACT CONNECTOR ASSEMBLY FOR IMPLANTABLE MEDICAL DEVICE

TECHNICAL FIELD

The present disclosure relates to electrical feedthroughs, and more particularly but without limitation to electrical feedthroughs for implantable medical devices (IMD's).

BACKGROUND

Electrical feedthroughs provide an electrical circuit path extending through a sealed container, such as a housing of an implantable medical device (IMD). Electrical feedthroughs include a conductive feedthrough pin that is electrically insulated from the container. In some examples, a feedthrough includes a ferrule and an insulator such as a hermetic glass or ceramic seal that supports the feedthrough pin within the ferrule.

Electrical feedthroughs for IMDs may be used in electrical medical devices such as electrical stimulators including neurostimulators and cardiac stimulators. Such electrical medical devices can be susceptible to electromagnetic interference (EMI). At certain frequencies, for example, EMI can inhibit stimulation signals from an electrical stimulator, such as pacing signals. For this reason, electrical feedthroughs may include a capacitor to shunt high frequency EMI from the feedthrough pin. In some examples, a capacitor is included within the ferrule such that the capacitor electrically contacts the feedthrough pin and the ferrule to shunt high frequency EMI away from the feedthrough pin.

In operation, a feedthrough capacitor permits passage of relatively low frequency electrical signals along the feedthrough pin, while shunting and shielding undesired high frequency interference signals to the ferrule, which may be physically and electrically coupled to a conductive housing of the device. Shunting high frequency interference signals away from the feedthrough pin mitigates the effects of EMI on a device by filtering high frequency signals from the feedthrough pin before the signals enter the interior of the device. This can limit adverse effects of EMI on the operations of an IMD, such as sensing, neurostimulation and/or cardiac stimulation therapy.

SUMMARY

This disclosure includes a variety of techniques that facilitate compact connector assemblies for IMDs. As one example, a connector assembly may include a plurality of feedthrough pins mounted in a staggered arrangement within an array plate of connector assembly.

In another example, each of the feedthrough pins may be electrically and mechanically bonded at an angle of less than 135 degrees to conductive strips of an electronics module assembly. In addition, the conductive strips of the electronics module assembly may be electrically and mechanically bonded at an angle of less than 135 degrees to conductors of a flexible circuit. The arrangement of the feedthrough pins, electronics module assembly and the flexible circuit may limit bending of conductors in the flexible circuit. By limiting bending of conductors in the flexible circuit, the connector assembly may not require the space otherwise necessary to provide a minimum bending radius of the flexible circuit.

In addition, a connector assembly may also include capacitors with a parallelogram-shaped profile. The capacitor may be mounted within a recess of an array plate of the connector assembly below the electronics module assembly and serves as a filter for multiple feedthrough pins.

In one example, this disclosure is directed to a connector assembly for an implantable medical device. The connector assembly comprises a plurality of feedthroughs mounted in a conductive array plate, each feedthrough in the plurality of feedthroughs including a feedthrough pin electrically isolated from the conductive array plate by an insulator. The connector assembly further comprises an electronic module assembly including a plurality of conductive strips set in a non-conductive block, wherein each of the plurality of conductive strips is in physical and electrical contact with a corresponding one of the feedthrough pins of the plurality of feedthroughs at a first set of electrical joints. The plurality of conductive strips is at an angle of less than 135 degrees relative to the feedthrough pins at the first set of electrical joints. The connector assembly further comprises at least one circuit, the circuit including a plurality of conductors corresponding to the plurality of feedthroughs. Each of the plurality of conductors of the circuit is in physical and electrical contact with a corresponding one of the conductive strips of the plurality of conductive strips of the electronic module assembly at a second set of electrical joints. The plurality of conductors is at an angle of less than 135 degrees relative to the plurality of conductive strips at the second set of electrical joints.

In another example, this disclosure is directed to an implantable medical device comprising a substantially sealed housing encasing control electronics, and a connector assembly that extends through the substantially sealed housing and provides electrical connections between the control electronics and a component of the implantable medical device located exterior to the substantially sealed housin. The connector assembly comprises a plurality of feedthroughs mounted in a conductive array plate, each feedthrough in the plurality of feedthroughs including a feedthrough pin electrically isolated from the conductive array plate by an insulator. The connector assembly further comprises an electronic module assembly including a plurality of conductive strips set in a non-conductive block, wherein each of the plurality of conductive strips is in physical and electrical contact with a corresponding one of the feedthrough pins of the plurality of feedthroughs at a first set of electrical joints. The plurality of conductive strips is at an angle of less than 135 degrees relative to the feedthrough pins at the first set of electrical joints. The connector assembly further comprises at least one circuit, the circuit including a plurality of conductors corresponding to the plurality of feedthroughs. Each of the plurality of conductors of the circuit is in physical and electrical contact with a corresponding one of the conductive strips of the plurality of conductive strips of the electronic module assembly at a second set of electrical joints. The plurality of conductors is at an angle of less than 135 degrees relative to the plurality of conductive strips at the second set of electrical joints.

In a different example, this disclosure is directed to a method of manufacturing a connector assembly for an implantable medical device. The method comprises positioning a plurality of feedthroughs within the apertures of an array plate, wherein each feedthrough in the plurality of feedthroughs includes an electrically conductive ferrule, an insulator located within the ferrule, and a feedthrough pin extending through the insulator such that it is electrically isolated from the ferrule by the insulator. The method further comprises electrically connecting and mechanically securing the ferrules of the feedthroughs to the array plate and positioning a capacitor including a set of apertures corresponding to more than one of the feedthrough pins over the feedthrough pins and into the recess of the array plate. The method further comprises electrically connecting and mechanically securing the capacitor to the array plate and to the more than one of the feedthrough pins such that the capacitor functions as a filter for the feedthrough pins in electrical contact with the capacitor, positioning an electronic module assembly including a set of conductive strips corresponding to more than one of the feedthrough pins over the feedthrough pins such that the capacitor is positioned between the electronic module assembly and the array plate, and electrically connecting and mechanically securing each of the feedthrough pins to the corresponding conductive strip in the electronic module assembly to form a first set of electrical joints. The plurality of conductive strips is at an angle of less than 135 degrees relative to the feedthrough pins after forming the first set of electrical joints. The method further comprises positioning at least one circuit, the circuit including a plurality of conductors corresponding to the plurality of feedthroughs, adjacent to a corresponding one of the conductive strips of the plurality of conductive strips of the electronic module assembly, and electrically connecting and mechanically securing each of the plurality of conductors of the circuit to the corresponding one of the conductive strips of the plurality of conductive strips of the electronic module assembly to form a second set of electrical joints. The plurality of conductors is at an angle of less than 135 degrees relative to the plurality of conductive strips after forming the second set of electrical joints The details of one or more examples of this disclosure are set forth in the accompanying drawings and the description below. Other features, objects, and advantages will be apparent from the description and drawings, and from the claims.

BRIEF DESCRIPTION OF DRAWINGS

FIGS. 4A-4C illustrate an array plate including apertures to receive unipolar feedthroughs of the compact connector assembly shown in FIG. 1.

FIG. 5 illustrates a unipolar feedthrough of the compact connector assembly shown in FIG. 1.

FIG. 6 illustrates a ground pin of the compact connector assembly shown in FIG. 1, the ground pin being size for mounting to a unipolar feedthrough aperture of the array plate shown in FIGS. 4A-4C.

DETAILED DESCRIPTION

Figure 1:
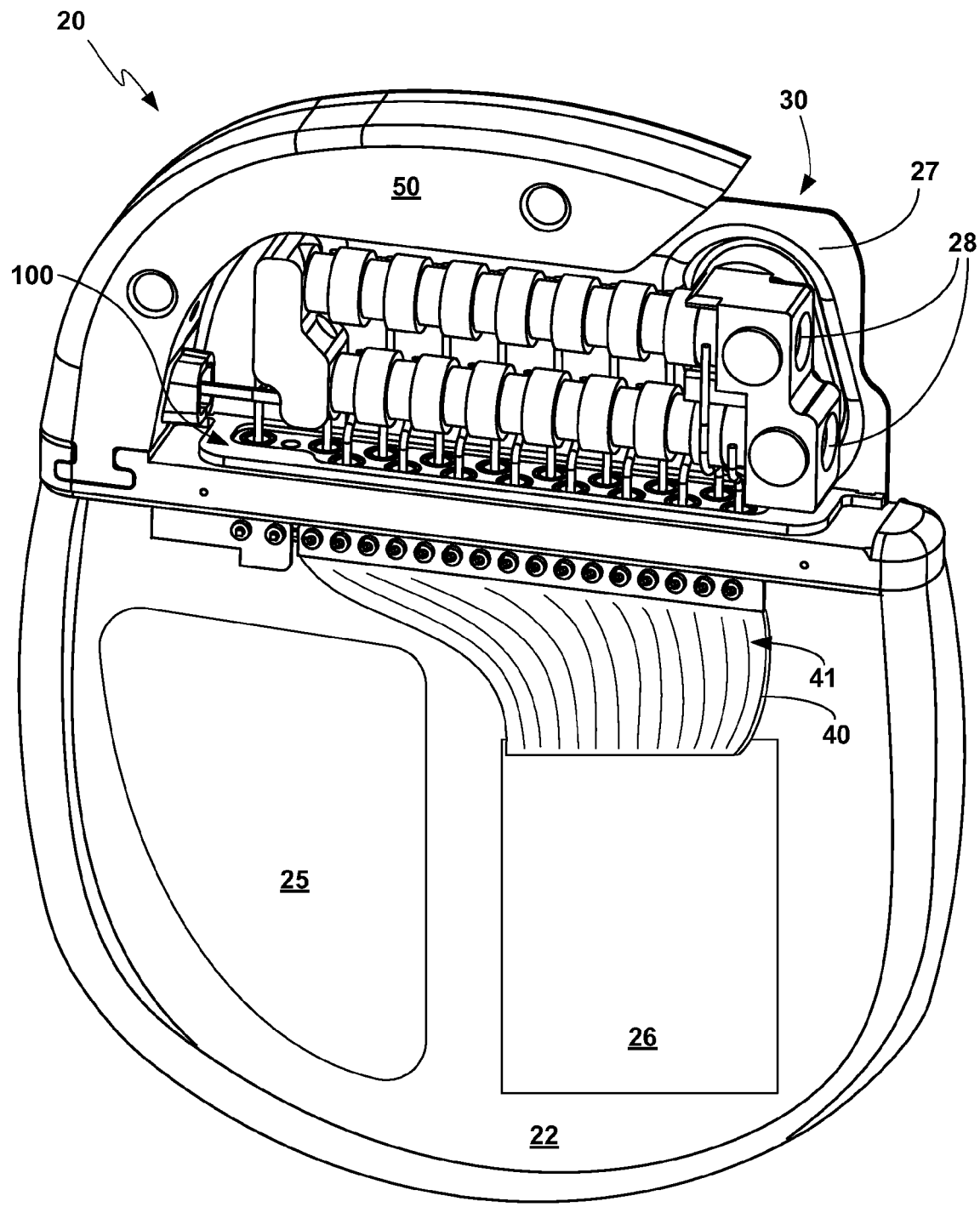
FIG. 1 illustrates a perspective view of an IMD including an example compact connector assembly.

FIG. 1 illustrates IMD 20, which includes connector assembly 100. IMD 20 provides one or more medical therapies to a patient and/or performs sensing functions. In some examples, IMD 20 may be an implantable electrical stimulator and provide an electrical stimulation therapy, such as a cardiac stimulation therapy, neurostimulation therapy, a deep brain stimulation therapy, a cochlear stimulation therapy, a pelvic stimulation therapy, a peripheral nerve stimulation therapy, and/or a gastric stimulation therapy. In the example of cardiac stimulation therapy, the cardiac stimulation therapy provided by IMD 20 may include a cardiac pacing therapy, a cardioversion therapy, and/or a defibrillation therapy. IMD may also perform sensing functions such as patient temperature sensing, pressure sensing, EKG sensing or other sensing functions. Exemplary IMDs that may be adapted to include a compact connector assembly as disclosed herein include, as examples and without limitation, the Medtronic CONCERTO™, SENSIA™, VIRTUOSO™, RESTORE™, and RESTORE ULTRA™ devices, sold by Medtronic, Inc. of Minneapolis, Minn.

IMD 20 includes electrical components to facilitate the medical therapy and/or sensing functions. For example, the electrical components may include one or more of a processor, stimulation generator, switch matrix, telemetry circuitry, memory, power supply, such as one or more rechargeable or non-rechargeable batteries and/or capacitors, and other components.

IMD 20 includes a substantially sealed housing 22. Substantially sealed housing 22 includes a case formed from a biocompatible material, and may be formed from a conductive material including titanium or stainless steel. Connector assembly 100 provides electrical connections between the components within the substantially sealed housing, such as power device 25 and controller assembly 26, and the components outside the substantially sealed housing, including connector body 27 and antenna 50. Power device 25, may include one or more batteries and/or capacitors. Connector body 27 and antenna 50 are located outside the substantially sealer housing.

Controller assembly 26 may include a circuit board having a processor, memory, transmitter, receiver, and/or other appropriate portions. Connector body 27 may extend from or be integrated with the case of substantially sealed housing 22. Connector body 27 includes ports 28 that interconnect with one or more connector terminals of one or more medical lead assemblies (not shown). In different examples, connector body 27 may include IS-1 connectors, IS-4 connectors or other suitable connectors. Each medical lead assembly includes one more conductors running the length of the medical lead assembly and sensing and/or stimulation electrodes that electrically connect to the connector terminals via the conductors. Connector body 27 further includes setscrews 30, which serve to secure the connector terminals of the medical lead assemblies within ports 28.

Antenna 50 is in electrical communication with an unfiltered feedthrough pin. Antenna 50 facilitates telemetry between IMD 20 and an external device such as a clinician programmer or a patient programmer when IMD 20 is implanted within a patient. For example, IMD 20 sends or receives therapy programs, therapy/or sensing history or other information via antenna 50.

Connector body 27 and antenna 50 are electrically connected to components within substantially sealed housing 22 via connector assembly 100. For example, feedthrough pins of connector assembly 100 may be spot-welded to a ball seal stack within connector body 27. As described in further detail with respect to FIGS. 2-9, connector assembly 100 includes a variety of features that facilitate a relatively high-density arrangement of electrically conductive paths through substantially sealed housing 22. As one example, connector assembly 100 includes a plurality of unipolar feedthroughs mounted in a staggered arrangement within an array plate of connector assembly 100. Unipolar feedthroughs include a single feedthrough pin supported within a ferrule by an insulator. Each of the feedthrough pins of the unipolar feedthroughs are electrically and mechanically connected at an angle of less than 135 degrees to conductive strips of an electronics module assembly. In addition, the conductive strips of the electronics module assembly are electrically and mechanically connected at an angle of less than 135 degrees to conductors of a flexible circuit.

The arrangement of the feedthrough pins, electronics module assembly and the flexible circuit limits bending of conductors in the flexible circuit between the electronics module assembly and components within housing 22, such as controller assembly 26, which can limit bending of conductors in the flexible circuit. For example, by limiting bending of conductors in the flexible circuit, the connector assembly does not require the space necessary to provide a minimum bending radius of the flexible circuit. A minimum bending radius of the flexible circuit may correspond to a bending radius which may adversely affect the integrity of conductors within the flexible circuit, e.g., due to fatigue loading.

In other examples, connector assembly 100 may connect to a circuit mounted on a relatively rigid substrate. Connector assembly 100 may facilitate using a circuit mounted on relatively rigid substrate because the design of connector assembly 100 does not require the circuit itself to bend within the IMD housing.

In addition, connector assembly 100 also includes two capacitors with parallelogram-shaped profiles. Each capacitor is mounted within a recess of the array plate of connector assembly 100 below the electronics module assembly and serves as a filter for multiple feedthrough pins, e.g., to mitigate electromagnetic interference. The shape of the capacitors allows the capacitors to be mounted in only one orientation within the recess of the array plate, i.e., "keyed," which precludes mounting the capacitors upside-down during the assembly of connector assembly 100, and which may simplify the manufacturing process and reduce mistakes during manufacturing.

Figure 2:
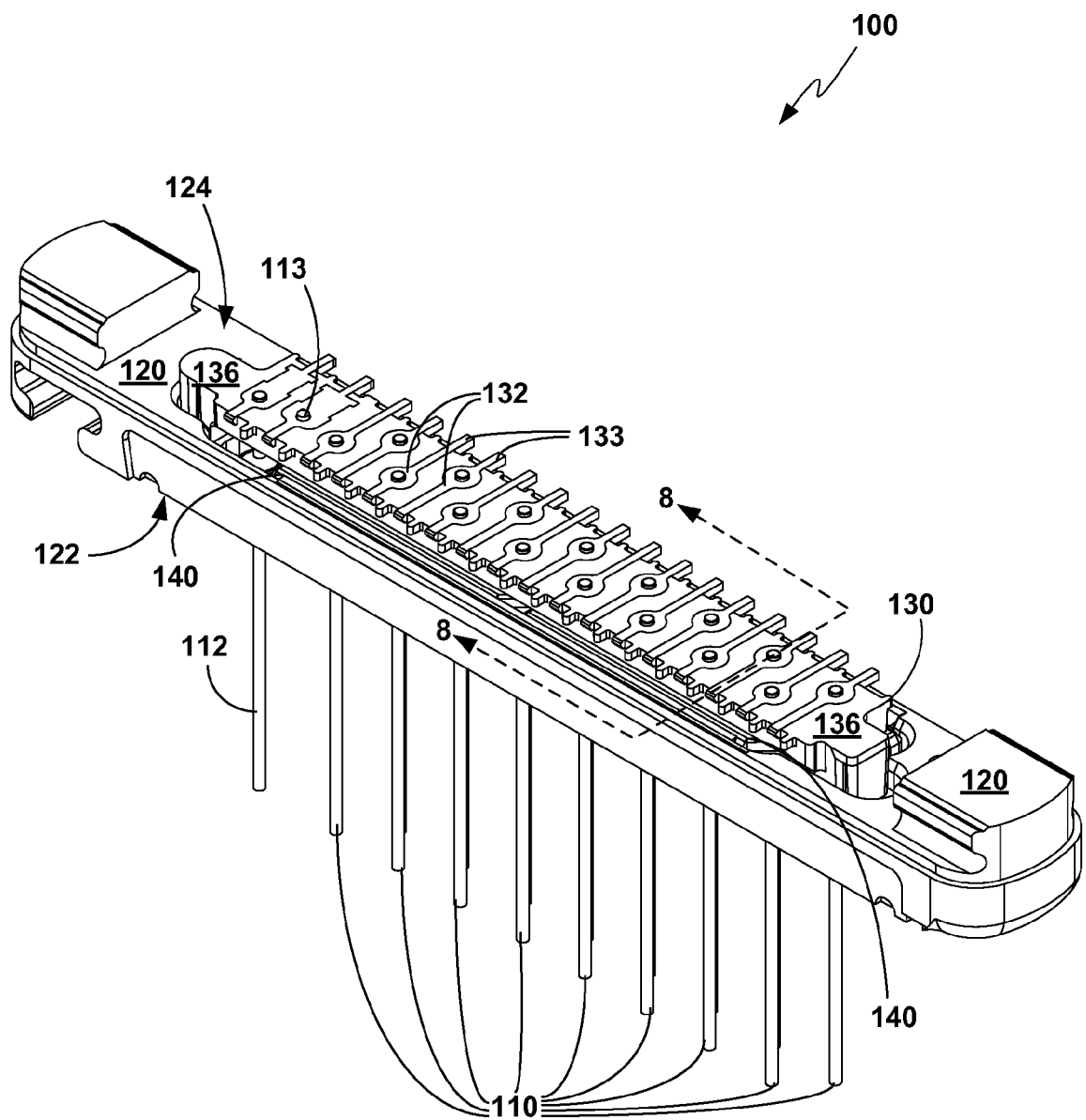
FIG. 2 illustrates a perspective view of the compact connector assembly shown in FIG. 1.
Figure 3:
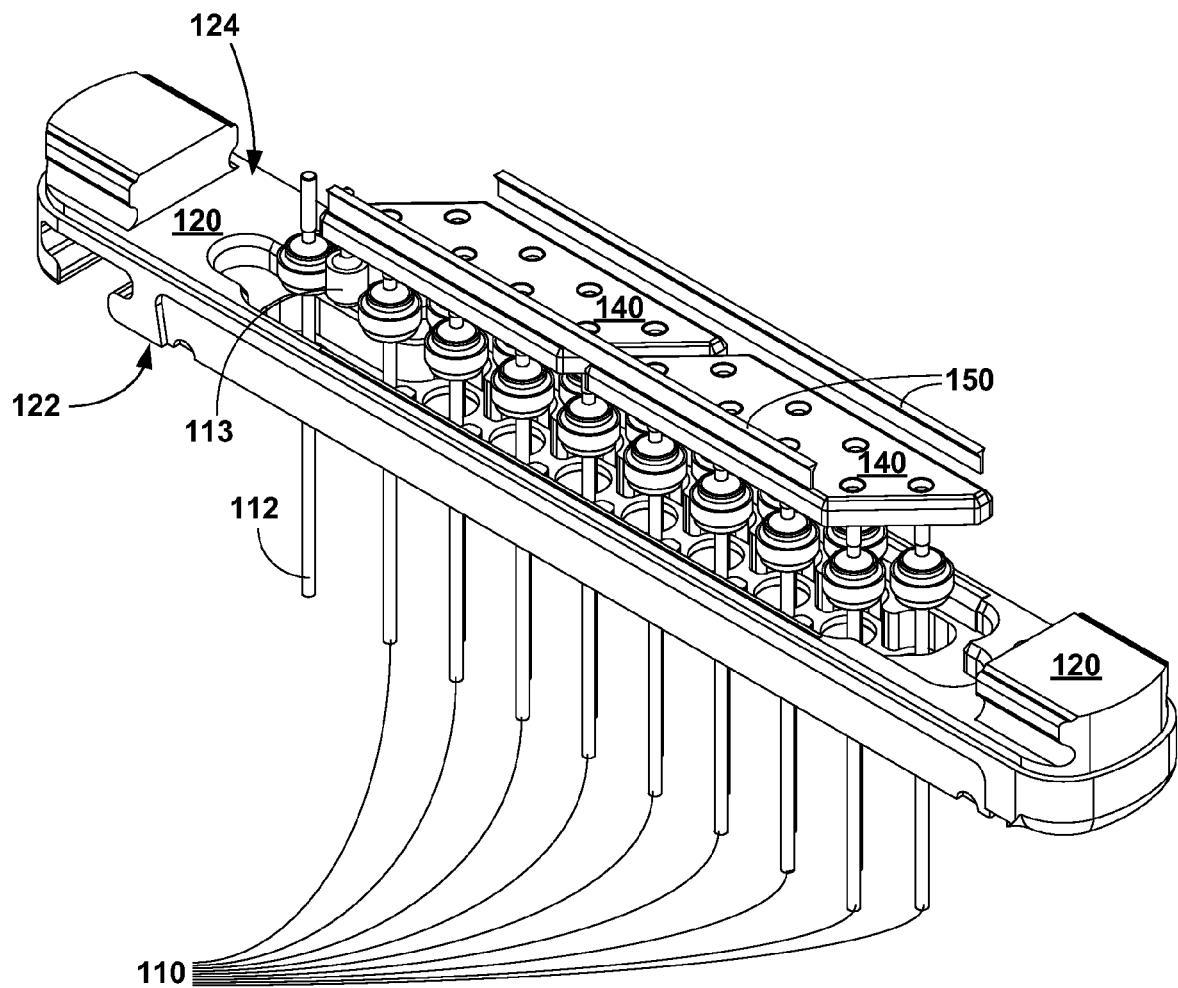
FIG. 3 illustrates an exploded view of the compact connector assembly shown in FIG. 1 without an electronic module assembly.

FIG. 2 illustrates connector assembly 100 in further detail, whereas FIG. 3 illustrates an exploded view of connector assembly 100 without electronic module assembly 130. Connector assembly 100 includes conductive array plate 120. Unipolar feedthroughs 110 are mounted within conductive array plate 120 and are filtered by parallelogram-shaped capacitors 140. Unfiltered feedthrough 112 is substantially similar to unipolar feedthroughs 110 and is also mounted within conductive array plate 120; however, unfiltered feedthrough 112 is not in electrical communication with parallelogram-shaped capacitors 140. Ground pin 113 is also mounted within conductive array plate 120. Conductive array plate 120 is shown in further detail in FIGS. 4A-4C, whereas a unipolar feedthrough 110 is shown in further detail in FIG. 5 and ground pin 113 is shown in further detail FIG. 6. In addition, a parallelogram-shaped capacitor 140 is shown in further detail in FIGS. 7A-7C. FIG. 8 illustrates a cross-sectional view of connector assembly 100 at cross-section 8-8 as indicated in FIG. 2.

Figure 4A:
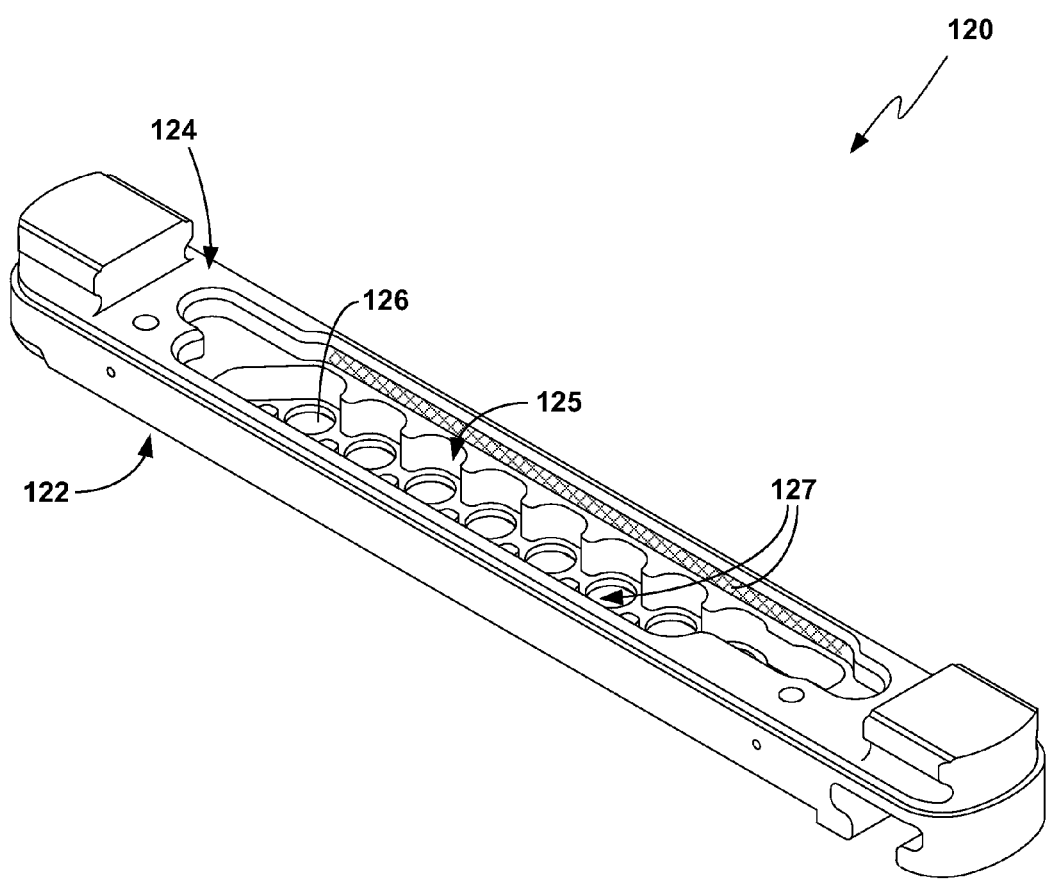

As shown in FIGS. 4A-4C, conductive array plate 120 includes recess 125 to receive feedthroughs 110, 112, ground pin 113 and capacitors 140. As best illustrated in FIG. 4C, recess 125 includes a lower portion 129 to receive feedthroughs 110, 112 and ground pin 113 and an upper portion 128 to receive capacitors 140.

Apertures 126 are located within the lower portion 129 of recess 125 and are configured to orient feedthroughs 110, 112 and ground pin 113 in a substantially common direction. In addition, apertures 126 are arranged in substantially straight and substantially parallel rows 176, 178. Apertures 126 are staggered within rows 176, 178. As one example, apertures 126 may be equally staggered such that an aperture 126 within row 176 is equidistant to the two closest apertures 126 within row 178. The staggered arrangement of apertures 126 within rows 176, 178 reduces the distance between rows 176, 178 necessary to prevent arcing between the feedthrough pins. Depending on the voltage between adjacent feedthrough pins 160, feedthrough pins 160 may need to be spaced a minimum of 55 mils (0.055 inches) from each other to prevent arcing between the feedthrough pins. By staggering feedthrough pins 160 in row 176 relative to feedthrough pins 160 in row 178, row 176 can be closer than 55 mils (0.055 inches) to row 178. This allows connector assembly 100 to be thinner than if feedthrough pins 160 in row 176 were aligned with feedthrough pins 160 in row 178.

When feedthrough 100 is mounted on an IMD, such as IMD 20 (FIG. 1), outer surface 122 of feedthrough 100 is external to the internal environment of substantially sealed housing 22, whereas inner surface 124 is located within the internal environment of substantially sealed housing 22. Outer surface 122 and inner surface 124 are indicated with respect to conductive array plate 120 in FIGS. 4A-4C. The reference numerals for outer surface 122 and inner surface 124 are used throughout FIGS. 2-8 to indicate portions of components located externally to the internal environment of substantially sealed housing 22 (122) and to indicate portions of components located within the internal environment of substantially sealed housing 22 (124).

One unipolar feedthrough 110 is illustrated in FIG. 5. In addition, an unfiltered feedthrough 112 may be substantially similar to unipolar feedthrough 110 as illustrated in FIG. 5. Unipolar feedthrough 110 includes feedthrough pin 160 and electrically conductive ferrule 162, which are separated by an electrical insulator 164 located within aperture 163 of ferrule 162. As examples, insulator 164 may be a hermetic glass or ceramic seal that supports feedthrough pin 160 within ferrule 162. Electrically conductive ferrule 162 includes notch 121, which is configured to register with one of apertures 126 in recess 125 of array plate 120.

Gold brazing 166 forms a seal, such as a hermetic seal, between ferrule 162 and insulator 164. Similarly, gold brazing 168 forms a seal, such as a hermetic seal, between insulator 164 and feedthrough pin 160. In other examples, different seals may be used between ferrule 162, insulator 164 and feedthrough pin 160. In some examples, insulator 164 may be sputtered with niobium to facilitate bonding with gold brazing 166 and gold brazing 168.

Feedthrough pin 160 includes a coating 169, which may be located on either or both of the interior side 124 and the external side 122 of feedthrough pin 160. Coating 169 may improve electrical connections between the feedthrough pin and conductive strips 132 of electronics module assembly 130 and between the feedthrough pin and conductors of connector body 27 (FIG. 1). As one example, coating 169 may comprise gold sputtering.

Ground pin 113 is illustrated in FIG. 6. Ground pin 113 is sized similarly to unipolar feedthrough 110 such that it is configured to fit within one of apertures 126 within recess 126 of array plate 120 and be located adjacent to feedthroughs 110, 112. For example, ground pin 113 includes notch 114, which is configured to register with one of apertures 126 in recess 125 of array plate 120. Ground pin 113 is formed from a biocompatible metal, such as a stainless steel or titanium alloy. As one example, ground pin 113 may be machined from a solid piece of metal. When mounted within one of apertures 126 within recess 126 of conductive array plate 120, ground pin 113 is grounded to housing 22 (FIG. 1) via conductive array plate 120. Ground pin 113 also includes terminal 115, which is electrically and mechanically bonded to electronic module assembly 130 in a similar manner as feedthrough pins 160 are electrically and mechanically bonded to electronic module assembly 130.

Figure 7A:
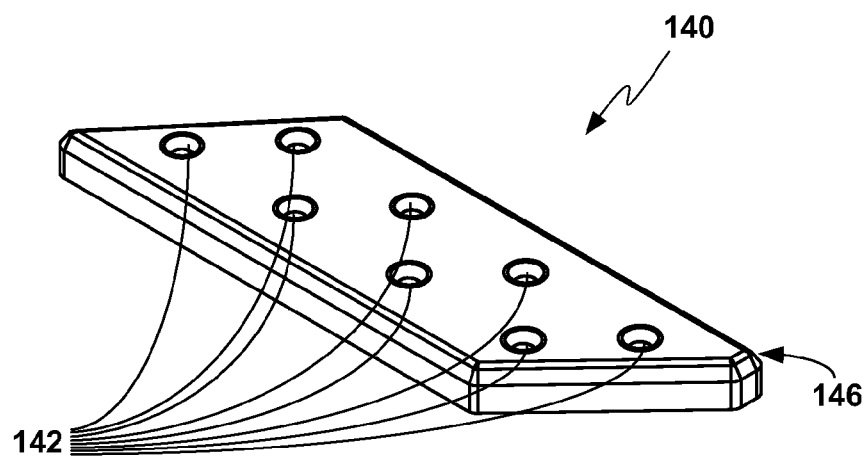
FIGS. 7A-7C illustrate a parallelogram-shaped capacitor of the compact connector assembly shown in FIG. 1.
Figure 7B:
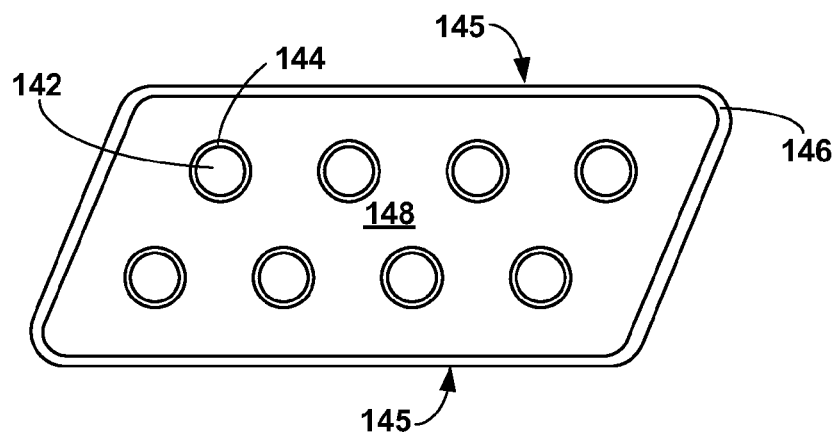
Figure 7C:
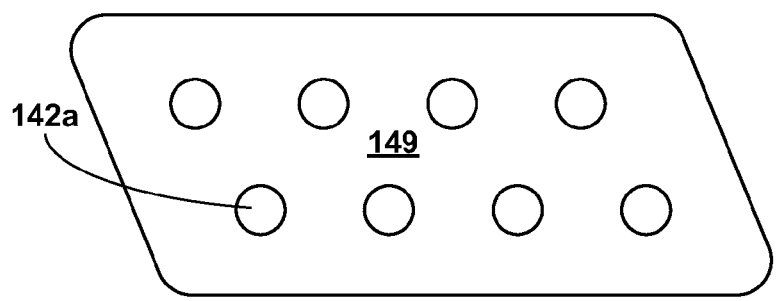
Figure 8:
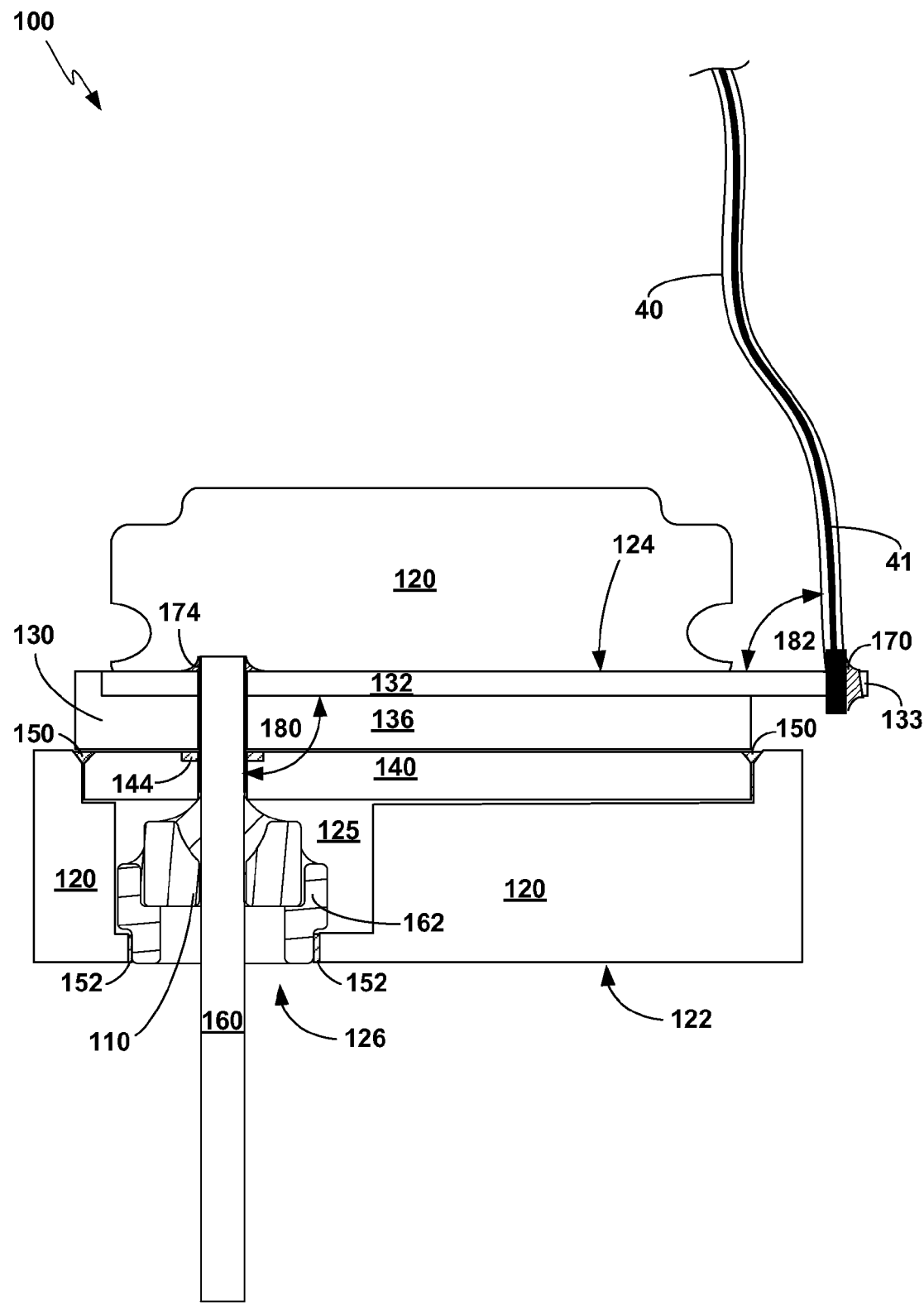
FIG. 8 is a cross-sectional view of the compact connector assembly taken across line 8-8 shown in FIG. 2, the cross-sectional view illustrating the electrical connection path of a single unipolar feedthrough.

FIGS. 7A-7C illustrate parallelogram-shaped capacitor 140. As previously mentioned, connector assembly 100 includes two parallelogram-shaped capacitors 140. Each of the parallelogram-shaped capacitors 140 within connector assembly 100 functions as a low-pass filter to provide shielding to a plurality of feedthroughs 110. Parallelogram-shaped capacitors 140 are positioned within upper portion 128 (FIG. 4C) of recess 125 of array plate 120 between electronic module assembly 130 and array plate 120. Within connector assembly 100, capacitors 140 are in electrical contact with array plate 120 and in electrical contact with more than one of feedthrough pins 160 such that capacitors 140 function as filters for the feedthrough pins in electrical contact with the capacitors.

Capacitor 140 includes a set of apertures 142 corresponding to the feedthrough pins in electrical contact with the capacitor 140 within connector assembly 100. Capacitor 140 includes upper side 148 and lower side 149. Apertures 142 extend from upper side 148 through lower side 149. As indicated on one of apertures 142 in FIG. 7B, capacitor 140 includes annular members 144 of conductive material over upper side 148 and around each of apertures 142. Annular members 144 provide improved contact between capacitor 140 and a corresponding feedthrough pin 160. As one example, annular members 144 may comprise sputtered gold. Techniques for providing a capacitor with annular members such as annular members 144 are described in further detail in U.S. Pat. Pub. No. 2010/0179606, titled "CAPACITOR FOR FILTERED FEEDTHROUGH WITH ANNULAR MEMBER," by Iyer, the entire contents of which are incorporated by reference herein.

Capacitor 140 has a parallelogram-shaped profile. The profile of capacitor 140 allows capacitor 140 to be mounted in only one orientation within the recess of the array plate, which precludes mounting capacitor 140 upside-down during the assembly of connector assembly 100, which may simplify the manufacturing process and reduce mistakes during manufacturing. As one example, to provide a different profile when positioned upside-down adjacent sides of the parallelogram-shaped profile may be of unequal lengths, i.e., the parallelogram-shaped profile is not a rhombus. In addition, the parallelogram-shaped profile is oblique in that the interior angles of the parallelogram-shaped profile are not right angles.

Within connector 100, solder joints 150 (FIG. 3) electrically connect capacitors 140 to array plate 120. In addition, solder joints (not shown) electrically connect annular members 144 to feedthrough pins 160. As one example, the solder joints between annular members 144 and feedthrough pins 160 may be formed by application of solder preforms upon the annular members of conductive material. The long sides of upper portion 128 (FIG. 4C) of recess 125 include gold sputtering 127 (FIG. 4A) to improve electrical contact between capacitors 140 and array plate 120. Similarly, the upper side of annular members 144 may include gold sputtering to improve electrical contact between capacitors 140 and feedthrough pins 160.

Electronic module assembly 130 (FIG. 2) is also mounted to array plate 120. Electronic module assembly 130 includes conductive strips 132. Feedthroughs 110, 112 and ground pin 113 are electrically and mechanically bonded to one of conductive strips 132 at a first set of contact pads. Conductive strips 132 further include a second set of contact pads 133, contact pads 133 being configured to electrically and mechanically connect to flexible circuit 40 as shown in FIG. 1 and FIG. 8.

Electronic module assembly 130 includes a plurality of conductive strips 132 set in a non-conductive block 136. Each of the plurality of conductive strips 132 is in physical and electrical contact with a corresponding one of feedthrough pins 160 feedthroughs 110, 112. In some examples, the plurality of conductive strips 132 may be formed from one or more metal stampings, such as a gold-plated nickel stamping. In addition, in some examples, non-conductive block 136 may be an overmold that fixes the position of conductive strips 132 relative to each other within electronic module assembly 130.

FIG. 8 illustrates cross section 8-8 of connector assembly 100 as indicated in FIG. 2. In particular, FIG. 8 illustrates the electrical connection path including a single one of unipolar feedthroughs 110. The electrical connection path shown in FIG. 8 is representative of the electrical connection paths associated with unipolar feedthroughs 110 in connector assembly 100.

As shown in FIG. 8, unipolar feedthrough 110 is electrically and mechanically bonded to array plate 120 via bonding 152. In different examples, bonding 152 may include soldering, brazing or welding, such as laser welding. Bonding 152 serves to seal ferrule 162 to array plate 120 filling aperture 126. Thus, bonding 152 helps maintain the integrity of substantially sealed housing 22 (FIG. 1).

Unipolar feedthrough 110 includes feedthrough pin 160. The portion of feedthrough pin 160 on the outer surface 122 of housing 22 is in electrical contact with contacts within ports 28 of connector body 27 (FIG. 8).

Feedthrough pin 160 is also in electrical contact with capacitor 140 via annular ring 144. As previously mentioned, capacitor 140 serves as a low-pass filter for feedthrough pin 160 and is also in electrical contact with array plate 120 vie solder joints 150. More specifically, capacitor 140 permits passage of relatively low frequency electrical signals along feedthrough pin 160, while shunting and shielding undesired high frequency interference signals array plate 120, which may be physically and electrically coupled housing 22. Shunting high frequency interference signals away from feedthrough pin 160 mitigates the effects of EMI on IMD 20 by filtering high frequency signals from feedthrough pin 160 before the signals enter the interior of the device, which can interfere with components within the substantially sealed housing, such as power device 25 and controller assembly 26. This can limit adverse effects of EMI on the operations of IMD 20, such as sensing, electrical stimulation or other therapy.

Feedthrough pin 160 is in electrical and mechanical contact with conductive strip 132 of electronic module assembly 130 via a first joint 174. Joint 174 may be, e.g., a mechanical joint, a solder joint, a brazed joint, a weld joint, such as a laser weld joint or other joint that provides a suitable electrical connection between feedthrough pin 160 and conductive strip 132. Conductive strip 132 is at an angle 180 of less than 135 degrees relative to feedthrough pin 160 at joint 174. For example, angle 180 may be less than 120 degrees, less than 100 degrees, or even less than 95 degrees. As one specific example, angle 180 may be about 90 degrees.

Contact pad 133 of conductive strip 132 is in electrical and mechanical contact with a conductor of flex circuit 40 via a second joint 170. Joint 170 may be on an opposing end of conductive strip 132 as compared to feedthrough pin 160. Joint 170 may be, e.g., a mechanical joint, a solder joint, a brazed joint a weld joint, such as a laser weld joint or other joint that provides a suitable electrical connection between conductive strip 132 and the conductor of flex circuit 40. Conductive strip 132 is at an angle 182 of less than 135 degrees relative to feedthrough pin 160 at joint 170. For example, angle 182 may be less than 120 degrees, less than 100 degrees, or even less than 95 degrees. As one specific example, angle 182 may be about 90 degrees.

Feedthrough pin 160 extends away from substantially sealed housing 22, in about an opposite direction as compared to conductors 41 of flexible circuit 40, which extend within the internal environment of substantially sealed housing 22. The other feedthrough pins of connector assembly 100 include similar electrical connection paths to that shown in FIG. 8 such that joint 174 is one of a first set of joints and joint 170 is one of a second set of joints.

Figure 9:
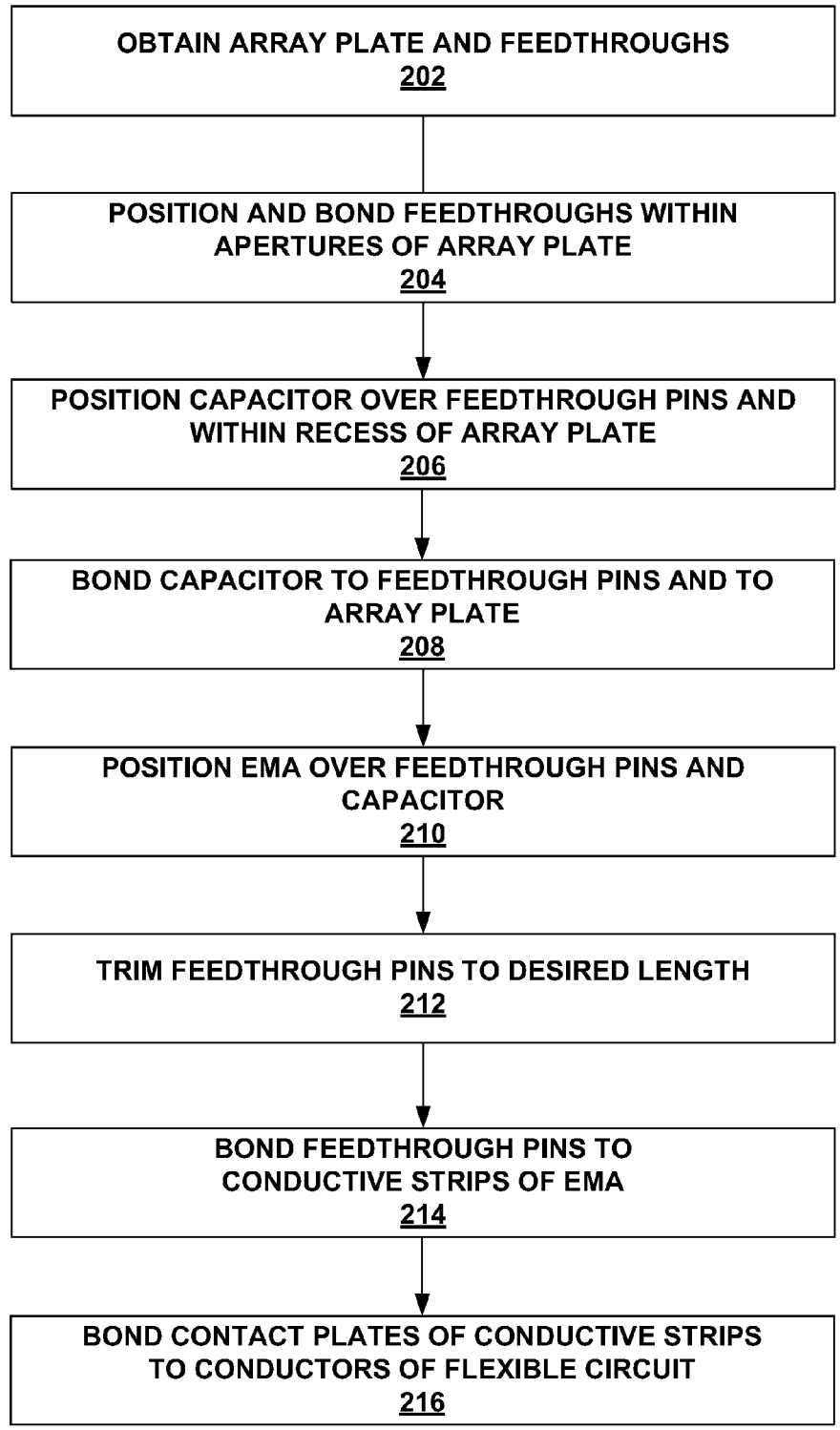
FIG. 9 is a flowchart illustrating techniques for manufacturing a connector assembly for an IMD.

FIG. 9 is a flowchart illustrating techniques for manufacturing a connector assembly for an IMD. For clarity, the techniques of FIG. 9 are described with respect to connector assembly 100 of IMD 20.

First, array plate 120 and feedthroughs 110 are obtained (202). Feedthroughs 110 are positioned with apertures 125 of array plate 120. Ferrules 162 of feedthroughs 110 are electrically and mechanically bonded to array plate 120 as positioned within apertures 126 (204). For example, ferrules 162 may be welded, such as laser welded to array plate 120. In other examples, ferrules 162 may be soldered or brazed to array plate 120. Unfiltered feedthroughs, such as unfiltered feedthrough 112 and/or ground pin 113 may also be electrically and mechanically bonded to array plate 120 within one of apertures 126, e.g., by welding brazing or soldering. Once feedthroughs 110 are mounted to array plate 120 within apertures 126, feedthrough pins 160 each extend within a substantially common direction, e.g., as shown in FIG. 2.

Next, two capacitors 140 are positioned over feedthrough pins 160 such that feedthrough pins 160 extend through apertures 142 of capacitors 140 and such that capacitors 140 fit within upper portion 128 (FIG. 4C) of recess 125 in array plate 120 (206). Capacitors 140 are electrically and mechanically bonded to array plate 130 via solder joints 150. Capacitors 140 are also electrically and mechanically bonded to feedthrough pins 160 at annular members 144 such that capacitors 140 functions as a filter for the feedthrough pins in electrical contact with the capacitor (208). With connector assembly 100, each capacitor 140 serves to shunt EMI from eight feedthrough pins 160. While connector assembly 100 includes two capacitors 140, in other examples a connector assembly may include any number of capacitors with parallelogram-shaped profiles.

In one example, electrically connecting and mechanically securing capacitors 140 to array plate 130 and to feedthrough pins 160 may include soldering capacitors 140 to array plate 130 and to feedthrough pins 160. In one particular example, soldering capacitors 140 to array plate 130 and to feedthrough pins 160 may include positioning solder preforms over the feedthrough pins and adjacent to annular members 144 and further positioning solder wire adjacent to the capacitor along major sides 145 (FIG. 7B) of the capacitors 140 and along the major sides of recess 125 in array plate 120. Capacitors include chamfer 146 along its edge at upper side 148 and, array plate 120 includes chamfer 127 (FIG. 4C) along the edge of recess 125. Chamfer 146 and chamfer 127 combine to form a groove to receive the solder wire.

An assembly including array plate 120, feedthroughs 110, capacitors 140, the solder preforms and the solder wire may then be heated to melt the solder preforms and the solder wire to solder capacitors 140 to array plate 120 and to feedthrough pins 160 of feedthroughs 110. As an example, the assembly may be placed into a chamber including only inert gases, such as argon, helium and/or nitrogen, and heated to a temperature between 300 and 350 degrees Celsius to melt the solder preforms and the solder wire.

Next, electronic module assembly 130, which includes a set of conductive strips 132 corresponding to feedthrough pins 160 is positioned over feedthrough pins 160 such that capacitors 140 are positioned between electronic module assembly 130 and array plate 120 (210). Electronic module assembly 130 may be formed by overmolding non-conductive block 136 on a stamping including conductive strips 132 and breaking off a removable tab of the stamping to electrically isolate conductive strips 132 from each other in the electronic module assembly 130, the removable tab being configured to maintain the relative positions of conductive strips 132 before overmolding non-conductive block 136 on the stamping.

Feedthrough pins 160 may optionally be trimmed to a desired length after positioning electronic module assembly 130 over feedthrough pins 160 (212). After the optional trimming, feedthrough pins 160 are electrically and mechanically bonded to the corresponding conductive strips 132 in electronic module assembly 130 to form a first set of electrical joints 174 (214). As shown in FIG. 2, conductive strips 132 include apertures to receive the feedthrough pins 160. In one example, feedthrough pins 160 may be soldered, such as laser soldered to conductive strips 132. In other examples, feedthrough pins 160 may be welded or brazed to conductive strips 132. In a further example, feedthrough pins 160 may be mechanically connected to conductive strips 132.

Finally, flexible circuit 40, which includes a plurality of conductors 41 corresponding to feedthroughs 110, is positioned adjacent to contact pads 133 of conductive strips 132 and the plurality of conductors of flexible circuit 40 are electrically and mechanically bonded to the corresponding conductive strips 132 opposite feedthrough pins 160 to form a second set of electrical joints 170 (216). In one example, conductors 41 of flexible circuit 40 may be soldered, such as laser soldered to conductive strips 132. In other examples, conductors 41 of flexible circuit 40 may be welded or brazed to conductive strips 132. In a further example, conductors of flexible circuit 40 may be mechanically connected to conductive strips 132.

Figure 10:
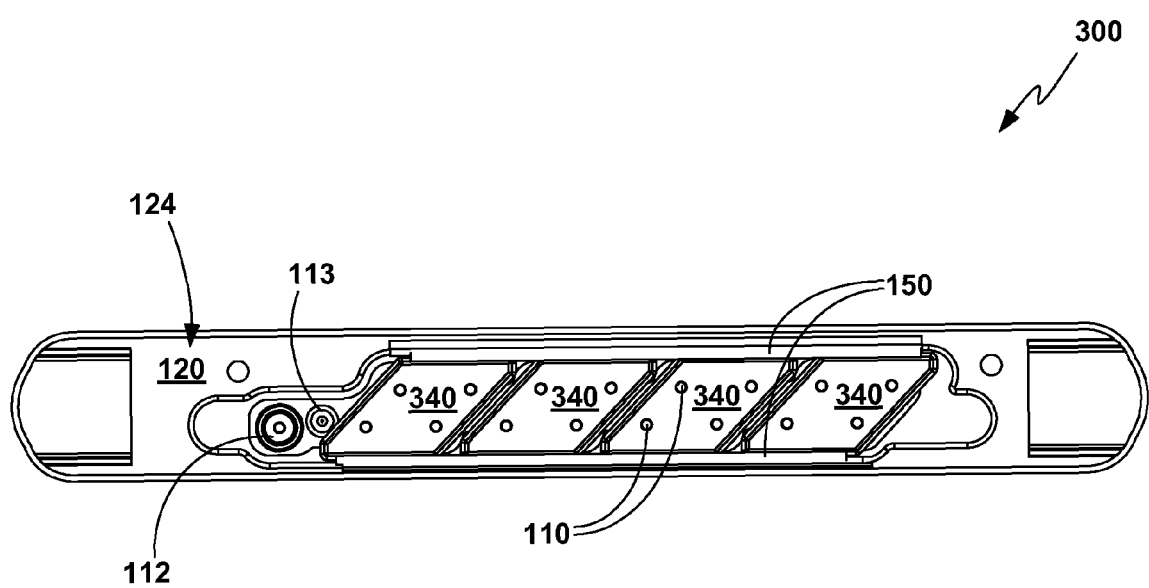
FIG. 10 illustrates a top view of a compact connector assembly including four parallelogram-shaped capacitors and without an electronic module assembly.

FIG. 10 illustrates a top view of compact connector assembly 300. Connector assembly 300 is similar to contact connector assembly 100, except that capacitors 340 are used in place of capacitors 140. Connector assembly 300 includes four parallelogram-shaped capacitors 340. Connector assembly 300 includes conductive array plate 120. Unipolar feedthroughs 110 are mounted within conductive array plate 120. Parallelogram-shaped capacitors 340 filter feedthroughs 110. Unfiltered feedthrough 112 is substantially similar to unipolar feedthroughs 110 and is also mounted within conductive array plate 120; however, unfiltered feedthrough 112 is not in electrical communication with parallelogram-shaped capacitors 340. Ground pin 113 is also mounted within conductive array plate 120. Connector assembly 300 further includes an electronic module assembly, such as electronic module assembly 130, but the electronic module assembly of connector assembly 300 is not shown in FIG. 10. For brevity, many details previously described with respect to connector assembly 100 are not discussed again with respect to connector assembly 300.

Connector assembly 300 includes four parallelogram-shaped capacitors 340. Each of the parallelogram-shaped capacitors 340 within connector assembly 300 functions as a low-pass filter to provide shielding to a plurality of feedthroughs 110. Specifically, each of the parallelogram-shaped capacitors 340 within connector assembly 300 functions as a low-pass filter to provide shielding to four feedthroughs 110. In contrast, each of the parallelogram-shaped capacitors 140 within connector assembly 100 functions as a low-pass filter to provide shielding to eight feedthroughs 110. In other examples, parallelogram-shaped capacitors may provide shielding for any number of feedthroughs including, e.g., one feedthrough, two feedthroughs, three feedthroughs, six feedthroughs, ten feedthroughs sixteen feedthroughs or any other number of feedthroughs. Further, different connector assemblies may include any number of parallelogram-shaped capacitors, each being substantially similar or each having a different shape or corresponding to a different bumber of feedthroughs. Furthermore, the capacitors of different connector assemblies may include more than two rows of apertures to receive a feedthrough pin or just one aperture to receive a feedthrough pin.

Parallelogram-shaped capacitors 340 are positioned within upper portion 128 (FIG. 4C) of recess 125 of array plate 120 between electronic module assembly 130 and array plate 120. Within connector assembly 300, capacitors 340 are in electrical contact with array plate 120 and in electrical contact with more than one of feedthrough pins 160 such that capacitors 340 function as filters for the feedthrough pins in electrical contact with the capacitors.

Capacitor 340 has a parallelogram-shaped profile. The profile of capacitor 340 allows capacitor 340 to be mounted in only one orientation within the recess of the array plate, which precludes mounting capacitor 340 upside-down during the assembly of connector assembly 300, which may simplify the manufacturing process and reduce mistakes during manufacturing. For example, the location of apertures for feedthroughs 110 within each of capacitors 340 may provide a "keyed" aspect to the profile of capacitor 340, even if the profile of capacitor 340 has a rhombus shape, i.e., four sides of equal length.

Within connector 300, solder joints 150 electrically connect capacitors 340 to array plate 120. In addition, solder joints (not shown) electrically connect capacitors 340 to feedthrough pins 160. As one example, capacitors 340 may include annular members such as those described with respect to capacitor 140.

Various examples of this disclosure have been described. These and other examples are within the scope of the following claims.

What is claimed is:

1. A connector assembly for an implantable medical device, the connector assembly comprising:
   a plurality of feedthroughs mounted in a conductive array plate, each feedthrough in the plurality of feedthroughs including a feedthrough pin electrically isolated from the conductive array plate by an insulator;
   an electronic module assembly including a plurality of conductive strips set in a non-conductive block, wherein each of the plurality of conductive strips is in physical and electrical contact with a corresponding one of the feedthrough pins of the plurality of feedthroughs at a first set of electrical joints,
   wherein the plurality of conductive strips is at an angle of less than 135 degrees relative to the feedthrough pins at the first set of electrical joints; and
   at least one circuit, the circuit including a plurality of conductors corresponding to the plurality of feedthroughs, wherein each of the plurality of conductors of the circuit is in physical and electrical contact with a corresponding one of the conductive strips of the plurality of conductive strips of the electronic module assembly at a second set of electrical joints,
   wherein the plurality of conductors is at an angle of less than 135 degrees relative to the plurality of conductive strips at the second set of electrical joints.

2. The connector assembly of claim 1,
   wherein the plurality of conductive strips is at an angle of about 90 degrees relative to the feedthrough pins at the first set of electrical joints, and
   wherein the plurality of conductors is at an angle of about 90 degrees relative to the plurality of conductive strips at the second set of electrical joints.

3. The connector assembly of claim 2, wherein the feedthrough pins extend in an about opposite direction as compared to the conductors of the circuit on opposing ends of the conductive strips of the electronic module assembly.

4. The connector assembly of claim 1,
   wherein the plurality of conductive strips are formed from one or more metal stampings, and
   wherein the non-conductive block comprises an overmold that fixes the position of the conductive strips relative to each other.

5. The connector assembly of claim 1,
   wherein the plurality of conductive strips include a first set of contact pads,
   wherein the feedthrough pins are soldered to the first set of contact pads to form the first set of electrical joints,
   wherein the plurality of conductive strips include a second set of contact pads, wherein the conductors of the circuit are soldered to the second set of contact pads to form the second set of electrical joints.

6. The connector assembly of claim 1, wherein the feedthrough pins extend though the array plate and the electronic module assembly is positioned within a recess of the array plate.

7. The connector assembly of claim 6, further comprising a capacitor,
   wherein the capacitor is positioned between electronic module assembly and the array plate,
   wherein the capacitor is within the recess of the array plate,
   wherein the capacitor is in electrical contact with the array plate and in electrical contact with more than one of the feedthrough pins such that the capacitor functions as a filter for the feedthrough pins in electrical contact with the capacitor,
   wherein the capacitor includes a set of apertures corresponding to the feedthrough pins in electrical contact with the capacitor, and
   wherein the capacitor has a parallelogram-shaped profile.

8. The connector assembly of claim 7,
   wherein the capacitor comprises an upper side and a lower side,
   wherein the apertures in the set of apertures extend from the upper side through the lower side,
   wherein the capacitor further comprises annular members of conductive material over the upper side and around each aperture in the set of apertures, and
   wherein the feedthrough pins in electrical contact with the capacitor are soldered to the apertures of the capacitor by application of solder preforms upon the annular members of conductive material.

9. The connector assembly of claim 7, wherein each of the feedthrough pins extends in a common direction, wherein the feedthrough pins are arranged in substantially straight and substantially parallel rows, and wherein the feedthrough pins in each row are staggered relative to the feedthrough pins in an adjacent row.

10. The connector assembly of claim 7, wherein the capacitor is a first capacitor, wherein the connector assembly includes a second capacitor, wherein the second capacitor has substantially the same shape as the first capacitor, and wherein the first and second capacitors are each in electrical contact with more than one of the feedthrough pins.

11. The connector assembly of claim 6, wherein each feedthrough in the plurality of feedthroughs includes an electrically conductive ferrule, wherein the insulator of each feedthrough is located within the ferrule, wherein the feedthrough pin of each feedthrough extends through the insulator and through the ferrule, wherein the array plate includes a plurality of apertures within the recess, each of the plurality of apertures being sized to receive the ferrule of one feedthrough in the plurality of feedthroughs, wherein the plurality of feedthroughs are positioned within the plurality of apertures within the recess.

12. The connector assembly of claim 11, further comprising a ground pin, wherein the ground pin is sized to fit within one of the plurality of apertures within the recess of the array plate, wherein the ground pin is positioned within one of the plurality of apertures within the recess, and wherein the ground pin is positioned adjacent to the plurality of feedthroughs.

13. The connector assembly of claim 1, wherein the circuit is a flexible circuit.

14. An implantable medical device comprising:
a substantially sealed housing encasing control electronics; and
a connector assembly that extends through the substantially sealed housing and provides electrical connections between the control electronics and a component of the implantable medical device located exterior to the substantially sealed housing, wherein the connector assembly comprises:
a plurality of feedthroughs mounted in a conductive array plate, each feedthrough in the plurality of feedthroughs including a feedthrough pin electrically isolated from the conductive array plate by an insulator;
an electronic module assembly including a plurality of conductive strips set in an non-conductive block, wherein each of the plurality of conductive strips is in physical and electrical contact with a corresponding one of the feedthrough pins of the plurality of feedthroughs at a first set of electrical joints,
wherein the plurality of conductive strips is at an angle of less than 135 degrees relative to the feedthrough pins at the first set of electrical joints; and
at least one circuit, the circuit including a plurality of conductors corresponding to the plurality of feedthroughs, wherein each of the plurality of conductors of the circuit is in physical and electrical contact with a corresponding one of the conductive strips of the plurality of conductive strips of the electronic module assembly at a second set of electrical joints,
wherein the plurality of conductors is at an angle of less than 135 degrees relative to the plurality of conductive strips at the second set of electrical joints.

15. The implantable medical device of claim 14, wherein the feedthrough pins extend in an about opposite direction as compared to the conductors of the circuit on opposing ends of the conductive strips of the electronic module assembly.

16. The implantable medical device of claim 14, wherein the plurality of conductive strips are formed from one or more metal stampings, and wherein the non-conductive block comprises an overmold that fixes the position of the conductive strips relative to each other.

17. The implantable medical device of claim 14, wherein the feedthrough pins extend though the array plate and the electronic module assembly is positioned within a recess of the array plate.

18. The implantable medical device of claim 17, further comprising a capacitor, wherein the capacitor is positioned between electronic module assembly and the array plate, wherein the capacitor is within the recess of the array plate, wherein the capacitor is in electrical contact with the array plate and in electrical contact with more than one of the feedthrough pins such that the capacitor functions as a filter for the feedthrough pins in electrical contact with the capacitor, wherein the capacitor includes a set of apertures corresponding to the feedthrough pins in electrical contact with the capacitor, and wherein the capacitor has a parallelogram-shaped profile.

19. The implantable medical device of claim 18, wherein the capacitor comprises an upper side and a lower side, wherein the apertures in the set of apertures extend from the upper side through the lower side, wherein the capacitor further comprises annular members of conductive material over the upper side and around each aperture in the set of apertures, and wherein the feedthrough pins in electrical contact with the capacitor are soldered to the apertures of the capacitor by application of solder preforms upon the annular members of conductive material.

20. The implantable medical device of claim 18, wherein the capacitor is a first capacitor, wherein the connector assembly includes a second capacitor, wherein the second capacitor has substantially the same shape as the first capacitor, and wherein the first and second capacitors are each in electrical contact with half of the feedthrough pins.

21. The implantable medical device of claim 17, wherein each feedthrough in the plurality of feedthroughs includes an electrically conductive ferrule, wherein the insulator of each feedthrough is located within the ferrule, wherein the feedthrough pin of each feedthrough extends through the insulator and through the ferrule, wherein the array plate includes a plurality of apertures within the recess, each of the plurality of apertures being sized to receive the ferrule of one feedthrough in the plurality of feedthroughs, wherein the plurality of feedthroughs are positioned within the plurality of apertures within the recess.

22. The implantable medical device of claim 21, further comprising a ground pin,
wherein the ground pin is sized to fit within one of the plurality of apertures within the recess of the array plate,
wherein the ground pin is positioned within one of the plurality of apertures within the recess, and
wherein the ground pin is positioned adjacent to the plurality of feedthroughs.

23. The implantable medical device of claim 14, wherein the component of the implantable medical device located exterior to the substantially sealed housing includes an antenna for telemetry when the implantable medical device is implanted within a patient.

24. The implantable medical device of claim 14, wherein the circuit is a flexible circuit.

25. A method of manufacturing a connector assembly for an implantable medical device, the method comprising:
positioning a plurality of feedthroughs within the apertures of an array plate, wherein each feedthrough in the plurality of feedthroughs includes an electrically conductive ferrule, an insulator located within the ferrule, and a feedthrough pin extending through the insulator such that it is electrically isolated from the ferrule by the insulator;
electrically connecting and mechanically securing the ferrules of the feedthroughs to the array plate;
positioning a capacitor including a set of apertures corresponding to more than one of the feedthrough pins over the feedthrough pins and into the recess of the array plate;
electrically connecting and mechanically securing the capacitor to the array plate and to the more than one of the feedthrough pins such that the capacitor functions as a filter for the feedthrough pins in electrical contact with the capacitor;
positioning an electronic module assembly including a set of conductive strips corresponding to more than one of the feedthrough pins over the feedthrough pins such that the capacitor is positioned between the electronic module assembly and the array plate;
electrically connecting and mechanically securing each of the feedthrough pins to the corresponding conductive strip in the electronic module assembly to form a first set of electrical joints,
wherein the plurality of conductive strips is at an angle of less than 135 degrees relative to the feedthrough pins after forming the first set of electrical joints;
positioning at least one circuit, the circuit including a plurality of conductors corresponding to the plurality of feedthroughs, adjacent to a corresponding one of the conductive strips of the plurality of conductive strips of the electronic module assembly; and
electrically connecting and mechanically securing each of the plurality of conductors of the circuit to the corresponding one of the conductive strips of the plurality of conductive strips of the electronic module assembly to form a second set of electrical joints;
wherein the plurality of conductors is at an angle of less than 135 degrees relative to the plurality of conductive strips after forming the second set of electrical joints.

26. The method of claim 25,
wherein electrically connecting and mechanically securing the capacitor to the array plate and to the more than one of the feedthrough pins comprises soldering the capacitor to the array plate and to the more than one of the feedthrough pins,
wherein soldering the capacitor to the array plate and to the more than one of the feedthrough pins comprises:
positioning solder preforms over the feedthrough pins;
positioning solder wire placed adjacent to the capacitor along major sides of the recess; and
heating an assembly including the array plate, the plurality of feedthroughs, the capacitor, the solder preforms and the solder wire to melt the solder preforms and the solder wire to solder the capacitor to the array plate and to the more than one of the feedthrough pins.

27. The method of claim 25,
wherein electrically connecting and mechanically securing each of the feedthrough pins to the corresponding conductive strip in the electronic module assembly comprises welding each of the feedthrough pins to the corresponding conductive strip in the electronic module assembly, and
wherein electrically connecting and mechanically securing each of the plurality of conductors of the circuit to the corresponding one of the conductive strips comprises soldering each of the plurality of conductors of the circuit to the corresponding one of the conductive strips of the plurality of conductive strips of the electronic module assembly.

28. The method of claim 25, further comprising trimming the feedthrough pins to a desired length after positioning the electronic module assembly over the feedthrough pins and before electrically connecting and mechanically securing each of the feedthrough pins to the corresponding conductive strips in the electronic module assembly.

29. The method of claim 25, wherein the conductive strips in the electronic module assembly include apertures to receive the feedthrough pins.

30. The method of claim 25,
wherein the electronic module assembly includes the plurality of conductive strips set in a non-conductive block, the method further comprising:
overmolding the non-conductive block on a stamping including each of the plurality of conductive strips; and
breaking off a removable tab of the stamping to electrically isolate the plurality of conductive strips from each other in the electronic module assembly, the removable tab being configured to maintain the relative positions of the plurality of conductive strips before overmolding the non-conductive block on the stamping.

31. The method of claim 25,
wherein each feedthrough in the plurality of feedthroughs includes an electrically conductive ferrule,
wherein the insulator of each feedthrough is located within the ferrule,
wherein the feedthrough pin of each feedthrough extends through the insulator and through the ferrule,
the method further comprising:
machining the array plate to form the recess and a plurality of apertures within the recess;
positioning each of the plurality of feedthroughs within the plurality of apertures within the recess; and
electrically connecting and mechanically securing the conductive ferrules of the plurality of feedthroughs to the array plate.

32. The method of claim 25, further comprising, after machining the array plate, sputtering gold along the major sides of the recess to form capacitor contact pads.

33. The method of claim 25, further comprising:
positioning a ground pin within one of the plurality of apertures within the recess of the array plate; and
electrically connecting and mechanically securing the ground pin to the array plate.

* * * * *